United States Patent [19]

Skiena

[11] Patent Number: 5,683,881

[45] Date of Patent: Nov. 4, 1997

[54] METHOD OF IDENTIFYING SEQUENCE IN A NUCLEIC ACID TARGET USING INTERACTIVE SEQUENCING BY HYBRIDIZATION

[75] Inventor: Steven S. Skiena, Port Jefferson, N.Y.

[73] Assignee: Biota Corp., Locust Valley, N.Y.

[21] Appl. No.: 546,423

[22] Filed: Oct. 20, 1995

[51] Int. Cl.[6] .................... C12Q 1/68; G01N 33/48; C07H 21/04

[52] U.S. Cl. .................. 435/6; 436/94; 436/501; 436/808; 935/77; 935/78; 536/24.3

[58] Field of Search .................. 435/6, 91.1, 91.2; 935/77, 78; 436/94, 501, 808; 536/24.33, 24.32, 23.1

[56] References Cited

U.S. PATENT DOCUMENTS 5,002,867  3/1991  Macevicz ........................... 435/6

OTHER PUBLICATIONS

Chetverin and Kramer Bio/Technology 12:1093–1099 Nov. 1994.
Skiena and Sundaram J. Computational Biology 2(2):333–353 Summer 1995.
Drmanac et. al. Genomics 4:114–128 (1989).
Broude et. al. Proceedings of the National Academy of Science, USA 91:3072–3076 (Apr. 1994).

Primary Examiner—W. Gary Jones
Assistant Examiner—Debra Shoemaker

[57] ABSTRACT

A new approach is proposed for sequencing by hybridization (SBH), which uses interaction to dramatically reduce the number of oligonucleotides used for de novo sequencing of large DNA fragments, while preserving the parallelism which is the primary advantage of SBH. In particular, a series of rounds is performed, starting from an initial fixed oligonucleotide array, of hybridizing a target sample against an array, and then designing a new oligonucleotide array in response to the results of the rounds to date, until the sequence is determined.

14 Claims, 3 Drawing Sheets

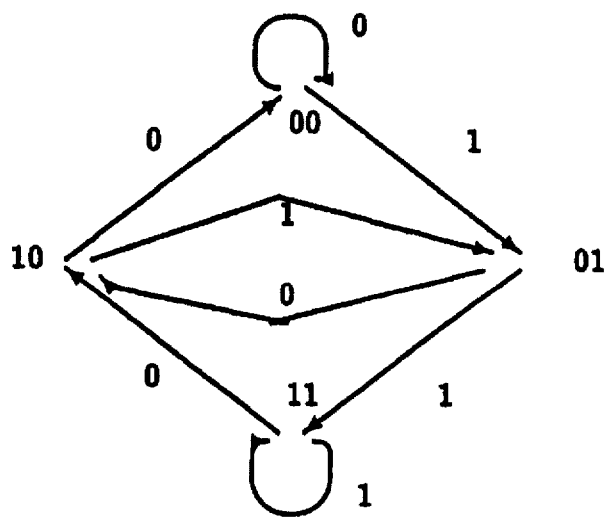
FIG. 1
FIG. 2A
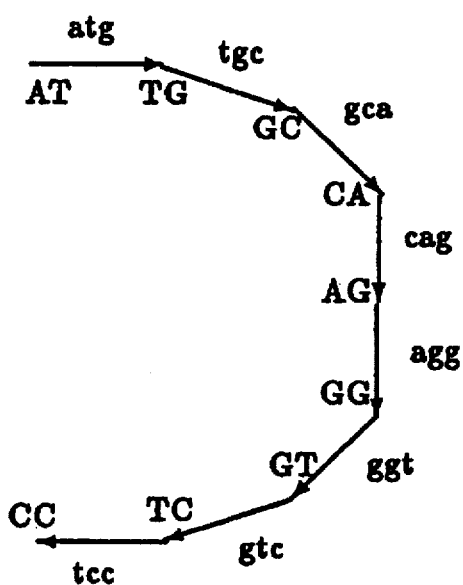
W = atgcaggtcc
FIG. 2B
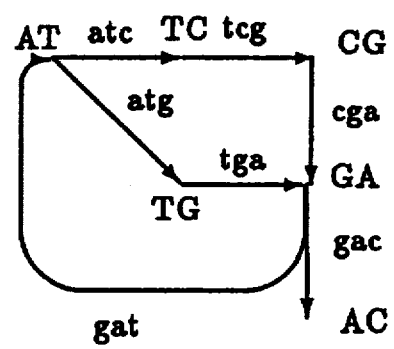
w1 = atcgatgac
w2 = atgatcgac

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 10 nucleotides
( B ) TYPE: nucleic acid
( C ) STRANDEDNESS: single
( D ) TOPOLOGY: linear ( x i ) SEQUENCE DESCRIPTION: SEQ ID NO: 1:

ATGCAGGTCC                                     10

METHOD OF IDENTIFYING SEQUENCE IN A NUCLEIC ACID TARGET USING INTERACTIVE SEQUENCING BY HYBRIDIZATION

BACKGROUND OF THE INVENTION

1. Field of the Invention

This invention relates generally to a method of determining the sequence of a nucleic acid by hybridization against multiple oligonucleotide probes, and more particularly, to a method of determining the sequence of a double or single stranded deoxyribonucleic acid (DNA) by interactive hybridization against multiple oligonucleotide probes.

2. Description of Related Art

The ability to determine nucleic acid sequences is critical for understanding the function and control of genes and for applying many of the basic techniques of molecular biology. Sequencing the human genome and other model organisms was first made possible by the inventions of Sanger et. al. *Proc. Natl. Acad. Sci.* 74 5463–5467 (1977) and Maxam et. al. *Proc. Natl. Acad. Sci.* 74 560–564 (1977). The Sanger method has seen great advances including automation, but still, only 300 to 500 bases can be sequenced under optimum conditions.

Sequencing by hybridization (SBH) is a new and promising approach to DNA sequencing which offers the potential of reduced cost and higher throughput over traditional gel-based approaches. Strezoska, et.al. *Proc. Nat. Acad. Science USA* 88 10089–10093 (1991) first accurately sequenced 100 base pairs of a known sequence using hybridization techniques, although the approach was proposed independently by several groups, including Bains and Smith *A novel method for nucleic acid sequence determination* 135 303–307 (1988), Drmanac and Crkvenjakov U.S. Pat. No. 5,202,231, Fodor et. al. U.S. Pat. No. 5,424,186, Lysov, et.al *Dokl. Acad. Sci. USSR*303 1508- (1988), Macevicz U.S. Pat. No. 5,002,867, and Southern European Patent EP 0 373 203 B1 and IPN WO 93/22480. More recently, Crkvenjakov's and Drmanac's laboratories report sequencing a 340 base-pair fragment in a blind experiment (Pevzner and Lipshutz, 19*th Int. Conf. Mathematical Foundations of Computer Science*, Springer-Verlag LNCS 841 143–158 (1994)). All of the above articles and patents are incorporated herein in their entirety.

The classical sequencing by hybridization (SBH) procedure attaches a large set of single-stranded fragments or probes to a substrate, forming a sequencing chip. A solution of radiolabeled single-stranded target DNA fragments are exposed to the chip. These fragments hybridize with complementary fragments on the chip, and the hybridized fragments can be identified using a nuclear detector or a fluorescent/phosphorescent dye. Each hybridization (or the lack thereof) determines whether the string represented by the fragment is or is not a substring of the target. The target DNA can now be sequenced based on the constraints of which strings are and are not substrings of the target. The surveys Pevzner and Lipshutz, 19*th Int. Conf. Mathematical Foundations of Computer Science*, Springer-Verlag LNCS 841 143–158 (1994) and Chetverin and Kramer *Bio/Technology* 12 1093–1099 (1994) give an excellent overview of the current state of the art in sequencing by hybridization; biologically, technologically, and algorithmically.

Sequencing by hybridization is a new technique, still in the proof of concept stage. Beyond the promise of general sequencing, the technology shows particular potential for rapidly sequencing variants of previously sequenced molecules. Further, hybridization can provide an inexpensive procedure to confirm sequences derived using other methods.

TABLE 1

Characteristic length of unambiguously deciphered DNA fragment as a function of the size for classical and interactive SBH.

| Fragment Length | Classical SBH | | Interactive SBH | |
|---|---|---|---|---|
| | Probe Length | Size | Rounds | Total Size |
| 80 | 7 | 16,384 | 7 | 560 |
| 180 | 8 | 65,536 | 8 | 1,440 |
| 260 | 9 | 262,144 | 8 | 2,080 |
| 560 | 10 | 1,048,576 | 8 | 4,480 |
| 1300 | 11 | 4,194,304 | 9 | 11,700 |
| 2450 | 12 | 16,777,216 | 9 | 22,050 |

The most widely used sequencing chip design, the classical sequencing chip C(m), contains all $4^m$ single-stranded oligonucleotides of length m, although other, non-classical sequencing chip designs are possible. In C(8) all $4^8$=65,536 octamers are used. The classical chip C(8) suffices to reconstruct 200 nucleotide long sequences in only 94 of 100 cases (Pevzner, et.al. *J. Biomolecular Structure and Dynamics* 9 399–410 (1991)), even in error-free experiments. Unfortunately, as shown in Table 1 by the column labeled 'Classical SBH—size', the length of unambiguously reconstructible sequence grows slower than the size (ie. area) of the chip. Thus such exponential growth inherently limits the length of the longest reconstructible sequence by classical SBH, and the size required by any single, fixed sequencing array on moderate length sequences will overwhelm the economies of scale and parallelism implicit in performing thousands of hybridization experiments simultaneously when using classical SBH methods.

Other variants of SBH (including nested-strand SBH (Rubinov and Gelfand *J. Computational Biology* (1995)) and positional SBH (Broude, Sano, Smith and Cantor, Enhanced DNA Sequencing by Hybridization, *Proc. National Academy of Sciences* (1994) have been proposed to increase the resolving power of classical SBH. But these methods still require large arrays to sequence relatively few base pairs. Thus new sequencing concepts are required to overcome these problems such as illustrated by Table 1.

Several different technologies have been proposed to fabricate oligonucleotide arrays for SBH. Perhaps the most promising (Fodor, et. al. *Science* 251 767–773 (1991)) use photolithography techniques typical of the semiconductor industry to fabricate the array C(5) of 1024 peptides in only ten steps. Larger chips, such as the array C(8) of 65,384 8-mers, are currently being developed by Affymax Inc. using this procedure. By the analogy with the semiconductor industry, chip capacity can be expected to continue to grow exponentially for several years. Thus such technologies provide large scale arrays, but still have limited utility due to the problems illustrated by Table 1.

Reconstructing hybridization data is where the algorithmic aspect of sequencing by hybridization arises. The outcome of an experiment with a classical sequencing chip C(m) assigns to each of the $4^m$ strings a probability that it is a substring of the underlying sequence S. In an experiment without error, these probabilities will all be 0 or 1, so each m-nucleotide fragment of S is unambiguously identified. Under what conditions is the sequence uniquely characterized?

Although efficient algorithms do exist for finding the shortest string consistent with the results of a classical sequencing chip experiment, these algorithms have not proven useful in practice because previous SBH methods do not return sufficient information to sequence long fragments. In particular, Pevzner's algorithm for sequencing chip reconstruction (Pevzner *J. Biomolecular Structure and Dynamics*, 7 63–73 (1989)) is based on finding Eulerian paths in a subgraph of the de Bruijn digraph (de Bruijn, *Proc. Kon. Ned. Akad. Wetensch* 49 758–764 (1946)). For a given alphabet $\Sigma$ and length k, the de Bruijn digraph $G_k(\Sigma)$ will contain $|\Sigma|^{k-1}$ vertices, each corresponding to a (k–1)-length string on $\Sigma$. As shown in FIG. 1, there will be an edge from vertex u to v labeled $\sigma \in \Sigma$ if the string associated with v consists of the last k–2 characters of u followed by $\sigma$. In any walk along the edges of this graph, the label of each vertex will represent the labels of the last k–1 edges traversed. Accordingly, each directed edge (u, v) of this graph represents a unique string of length k, defined by the label of u followed by the label of (u, v).

Since the digraph is strongly connected, and the in-degree of each vertex equals its outdegree, there is an Eulerian cycle in the digraph, ie. a tour which visits each edge exactly once. Further, Eulerian cycles are algorithmically easy to find if they exist. The string defined by the labels of the edges traversed will be shortest string which contains every k-string on $\Sigma$ as a substring.

A hybridization experiment with the sequencing chip C(k) identifies which k-strings are and are not in S. For each string which is not, the appropriate edge from $G_k(\Sigma)$ is deleted. Any postman walk (an Eulerian path which is permitted to repeat edges) on the remaining graph is a possible sequence. If the remaining graph consists of a single Eulerian path, as in FIG. 2(a), then the sequence S is completely determined by C(k). However, whenever there is a single node of in- or out-degree two, S is not uniquely defined by the data, as is the case in FIG. 2(b). This is not an uncommon situation—for example C(8) suffices to reconstruct 200 nucleotide long sequences in only 94 of 100 cases (Pevzner, et.al. *J. Biomolecular Structure and Dynamics* 9 399–410 (1991)), even in error-free experiments.

For the foregoing reasons, there is a need for a sequencing method capable of sequencing large fragments at low cost. Thus the invention provides a novel method of interactive sequencing by hybridization with nucleic acid probes which includes a new procedure for the step of selecting a subsequent set of probes.

SUMMARY OF THE INVENTION

The present invention provides interactive sequencing by hybridization with nucleic acid probes and includes the step of selecting a subsequent set of probes using an adaptive, interactive algorithm. The inventor has previously studied reconstructing unknown strings with single substring probes (Skiena and Sundatum, *J. Computational Biology*, 2 333–353 (1995)), however such techniques are impractical for large scale DNA sequencing because they are inherently sequential. This invention presents the critical techniques which capture the combinatorial advantages of interaction to minimize the size of arrays needed for sequencing large DNA fragments, while preserving parallelism and minimizing the number of experimental rounds needed for sequencing. Interactive SBH was unexpected for two reasons: (1) the potential combinatorial advantages of the approach were not apparent until the detailed analysis presented in the 'description of the preferred embodiments', and (2) the technologies previously proposed for fabricating oligonucleotide arrays do not even suggest interaction without substantial additional cost and/or effort, complications with no apparent advantages prior to the analysis of (1).

I propose a new approach to sequencing by hybridization which permits the sequencing of arbitrarily large fragments of nucleic acids without the limitations of synthesising the inherently exponential content of fixed arrays, while retaining the advantages of hybridizing in a massively parallel fashion.

This approach uses interaction to reduce the required amount of synthesis, hybridization and analysis involved in determining the sequence of a nucleic acid. After beginning with the hybridization of a target to a prefabricated sequencing chip (such as C(8)), we take the results from this experiment and use them to design a customized sequencing chip to resolve any ambiguities that may have arisen from the target containing too many nucleic acids to be resolved on the original chip. We repeat this process until all the remaining ambiguities have been resolved, thus determining the complete sequence of the target.

The use of efficient algorithms in combination with hybridization of oligonucleotide arrays to the target allows the design of sequencing chips to complete the sequence using as few rounds of hybridization to chips of as few oligos as possible. The results of Table 1 demonstrate the success of our method, using less than ten rounds to reduce the total number of probes by several orders of magnitudes on fragments of reasonable size. Thus the potential savings increase very rapidly with the length of the fragment to be sequenced.

Furthermore, this invention provides a practical sequencing method using low cost, custom-designed sequencing chips. Continuing advances in chip fabrication technology add to making our method a practical approach to sequencing. The scanning strip technology reported in Wehnert, et al. *Nucleic Acids Research* 22 1701–1704 (1994) can be used to construct a wide variety of arrays on demand. Multiplexing the 64 channel synthesis chamber allows for the production of 4,096 unique oligonucleotides. The incorporation of photolithographic techniques for nucleic acid synthesis as reported in Fodor, et. al. *Science* 251 767–773 (1991) allows for a wide variety of chips to be made with greater control over the sequence of individual pixels.

Such methods allow for the production of customized sequencing chips with capacities of millions of oligonucleotides selected as the subsequent set of probes. This interactive method reduces the overall construction required. The result of combining the two is low cost, megabase de novo sequencing.

Further, other potential chip fabrication methods based on printing technologies, including laser scanning and ink-jet spraying, place no premium at all on using a static chip design. Such fabrication methods yield even greater cost advantages when coupled with this invention.

Consequently, one object of this invention of interactive sequencing by hybridization with nucleic acid probes is to select a subsequent set of probes in response to the results of the previous rounds of experiments. Another object is to avoid making probes whose outcome can be predicted given the results from having used previous probes. There are several basic approaches to the design of such probes—primarily based on constructing longer probes by extending or concatenating old probes, or constructing probes which traverse across branch points in the appropriate subgraph of the de Bruijn graph defined by previous probes. Several procedures for selecting subsequent probes are detailed in the description of preferred embodiments, but others will be clear to practitioners skilled in the art.

The ideas of interactive SBH can be generalized to sequencing multiple target strings. Our invention of interactive SBH with nucleic acid probes applicable to Crkvenjakov and Drmanac's target-down approach to SBH (U.S. Pat. No. 5,202,231) which uses one probe per round but achieves parallelism through multiple targets. Greater efficiency will result by selecting the subsequent hybridization probe in response to previous results instead of blindly using a fixed order.

Interactive SBH is potentially robust in the face of hybridization errors. Because of overlaps in the probes generated by the algorithms below, there should be no difficulty handling false-positive hybridizations. False negatives are more difficult to identify, but I have discovered that corroborating probes of putative terminating strings can be added in subsequent rounds to increase reliability. The length of our oligonucleotide probes (typically from 8–20) seems sufficient to minimize the problem of hybridization errors.

Although in the protocol outlined for interactive SBH, each synthesized sequencing chip is only used once, there is considerable potential to reuse chips and mask designs in sequencing mutant or homologous sequences, since the oligo content of these sequences is extremely similar.

Carrying this idea further, the total number of oligonucleotides used over the complete set of rounds is small enough to justify using this invention for the design of pre-fabricated sequencing chips, which seek to identify mutations in specific genes for diagnostic purposes. By making a chip which is the union of all of the probes made over all rounds for a specific sequence, it is guaranteed that any mutation will be detected, since if all questions are answered identically to the original sequence, the test sequence must be identical to the original. Further, the exact mutation should be identified in most cases, from the sequence of differences in the answers.

BRIEF DESCRIPTION OF THE DRAWINGS

These and other features, aspects, and advantages of the present invention will become better understood with regard to the following description, appended claims, and accompanying drawings where:

FIG. 1 shows the de Bruijn digraph $G_3(\{0, 1\})$.

FIG. 2a shows a sequence completely defined by an Eulerian path in its de Bruijn digraph. FIG. 2b shows a sequence which is not completely defined because of multiple Eulerian paths its de Bruijn digraph.

DESCRIPTION OF THE PREFERRED EMBODIMENTS

Figure 3:
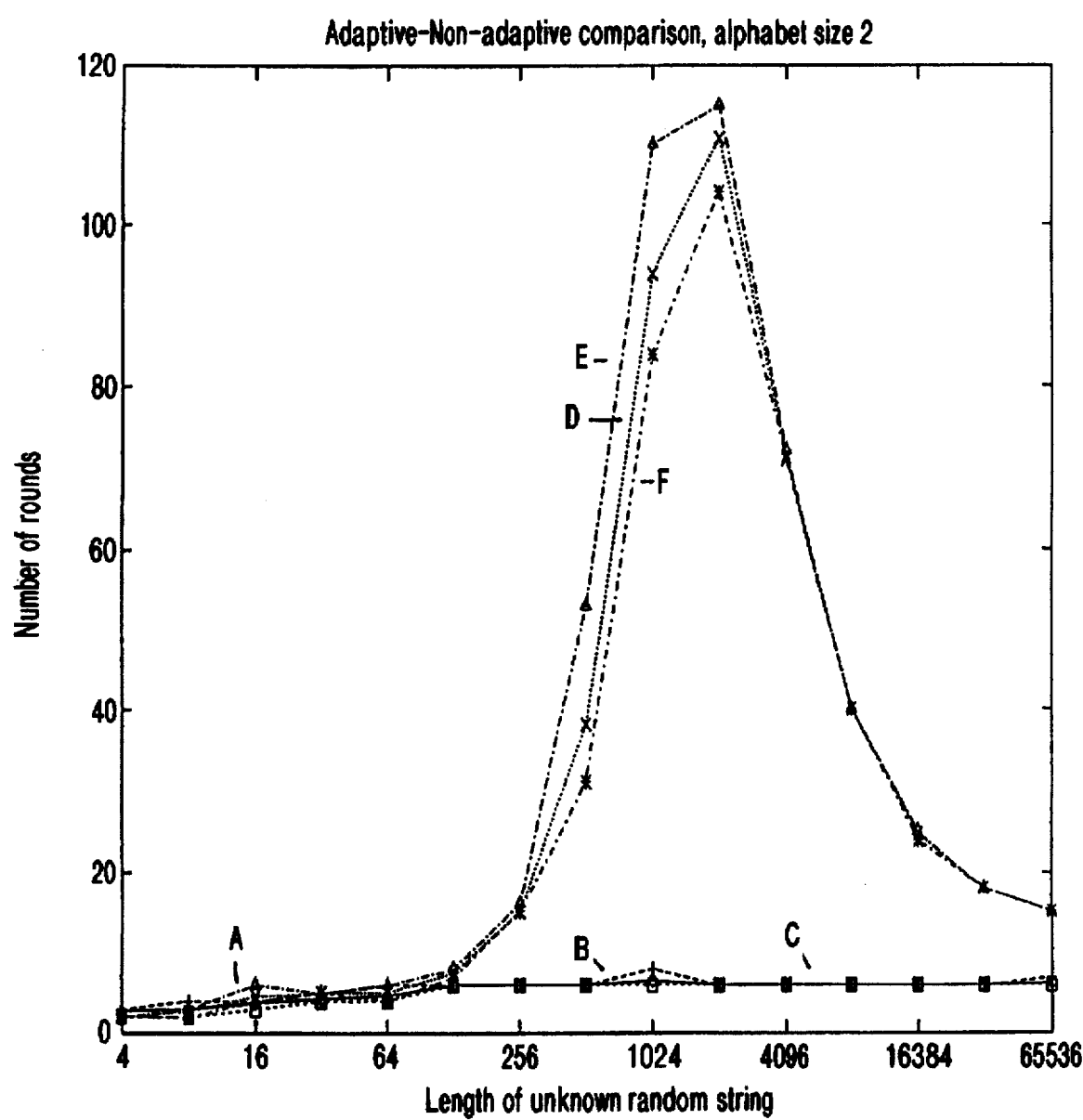
FIG. 3 shows the performance of two different adaptive probe algorithms on sequences over binary alphabets. The letters A, B, C, D, E, and F refer to the average number of rounds for the adaptive algorithm, the maximum number of rounds for the adaptive algorithm, the minimum number of rounds for the adaptive algorithm, the average number of rounds for the non-adaptive algorithm, the maximum number of rounds for the non-adaptive algorithm, and the minimum number of rounds for the non-adaptive algorithm, respectively.

The described versions of the present invention has many advantages as a method of nucleic acid sequencing, most notably the ability to determine large nucleic acid sequences at low cost.

The following terminology is used. By providing the probes, I mean the construction or assembly process taking a set of strings representing oligonucleotides and fabricating an equivalent array of nucleic acid probes. By hybridizing, I refer to the standard biochemical process of hybridization, as described in Drmanac and Crkvenjakov U.S. Pat. No. 5,202,231, Macevicz U.S. Pat. No. 5,002,867, and Southern European Patent EP 0 373 203 B1 and IPN WO 93/22480, which are incorporated by reference. By utilizing, I imply performing the laboratory experiment where the probes hybridize to the target. By identifying, I imply the process of analyzing the results of the experiment to determine which subset of probes hybridized to the target.

Probes are redundant if they provide only information about the sequence which is a consequence of the results of previous probes. A probe is non-redundant if it is not redundant. In specifying the construction of the non-redundant probes, I use the following terminology standard in discussions of character strings. The concatenation A+B of strings A and B is formed by appending A to B. If A=xyz and B=yzx, then A+B=xyzyzx. A overlaps B in a string S if S begins with A and ends with B and the length of S is less than that of A+B. Thus A overlaps B when S=xyzx. A is followed by B in S when S begins with A and ends with B. Thus A is followed by B in S=xyzaaayzx, as it is in both concatenation and overlap.

The following paper example illustrates an embodiment of the invention. Initially, prepare a fixed array of nucleic acid probes, say the classical chip C(2) consisting of all 16 2-mers. Hybridize the target against this first array, and identify which probes were positively hybridized with this target. For the purposes of this example, say AA, AT, CA, GC, GG, TG were the six positively hybridized probes, and AC, AG, CC, GA, CG, CT, GT, TA, TC, and TT were the ten negatively hybridized probes.

A combinatorial algorithm will now be applied to utilize the results of this experiment and design a second array. For the purposes of this example, the doubling algorithm (discussed below) will be used, which concatenates each pair of positively hybridized probes and eliminates any candidate which contains a negatively hybridized probe. Candidate probe AATG survives the test, since AT is a positively hybridized probe, where as candidate probe AAGG does not because it contains AG. All told, the following set of 16 nucleic acid probes will be selected as the second set of probes: AAAA, AAAT, AATG, CAAA, CAAT, CATG, ATGC, ATGG, GCAA, GCAT, GGGC, GGGG, TGCA, TGGC, and TGGG. Hybridize the target against this second array, and identify which probes were positively hybridized with this target. For the purposes of this example, say AAAA, AAAT, AATG, CAAA, ATGG, and GCAA were the six positively hybridized probes.

The same combinatorial algorithm will now be applied to utilize the results of these experiments and design a third array. The following set of eleven nucleic acid probes will be selected as the third set of probes: AAAAAAAA, AAAAAAAT, AAAAAATG, AAAAATGG, CAAAAAAA, CAAAAAAT, CAAAAATG, CAAAATGG, GCAAAAAA, GCAAAAAT, and GCAAAATG. Hybridize the target against this third array, and identify which probes were positively hybridized with this target. For the purposes of this example, say GCAAAATG and CAAAATGG were the only two positively hybridized probes.

The same combinatorial algorithm will now be applied to utilize the results of these experiments, revealing that no probes will be selected. The target sequence must be CGAAAATGG to be consistant with the results of all experiments, and so the target has been completely and successfully sequenced with this invention.

The hybridization arrays can be synthesized using a solution-channel device (Southern et al. *Genomics* 13 1008–1017 (1992)), an automated version of which has already been shown successful both for producing 64 unique oligonucleotides (Wehnert, et al. *Nucleic Acids Research* 22 1701–1704 (1994)) synthesized on an animated polypropylene substrate (Maston et al. *Analytical Biochemistry* 217 306–310 (1994)). The 64 channels can also be multiplexed to producing 4,096 unique oligonucleotides (Maston et al. *Analytical Biochemistry* 224 110–116 (1995)). The ultimate miniaturization of such techniques, however, is limited to the size of the channels, making an efficient method of producing select libraries rather than whole libraries a necessity.

The incorporation of photolithographic techniques for nucleic acid synthesis as reported in Fodor, et. al. *Science* 251 767–773 (1991) allows for a wide variety of high-density, miniaturized oligonucleotide arrays to be made with greater control over the sequence of individual pixels.

Preparation of the target molecule will involve providing samples suitable for hybridization while retaining information to reposition their sequence in the host genome. Shotgun methods have already been shown to be successful for assembling the genomes of simple free-living organisms, such as *Haeraophilus influenzae* (Fleischman, et al. *Science*269 496–512 (1995)). For more complex genomes, more ordered samples will be needed, such as those created by primer walking (Kieleczawa, et. al. *Science* 258 1787–1791 (1992)). PCR makes possible the amplification of many targets.

Hybridization to arrays involves the use of low stringency temperatures, such as 4° C. for 6 or 8-mers (Drmanac et al. DNA and *Cell Biology* 9 527–534 (1990)), and can also utilize chaotropic solvents to neutralize the differences in binding energy between AT and GC base pairs (Maskos and Southern *Nucleic Acids Research*21 4663–4669 (1993)). Detection of hybridization is a standard procedure to detect fluorescent or radioactive tags affixed to the target DNA.

I have found the following procedures particularly useful for the step of selecting the set of probes:

The Doubling Algorithm—This is a direct implementation of the worst-case $O(\log_2 n)$ round algorithm discussed below. Given the set of all 1-substrings of the unknown sequence S, we ask all 2l-length probes formed by concatenating two substrings together, provided all the l-substrings of the prospective probe are l-substrings of S. If there are $M_i$ probes in the ith meta-round which survive this test, they are asked in $\lceil M/n \rceil$ rounds of n probes per round. The first round consists of the classical chip $C(\lceil \log_2 n \rceil)$.

For example, if S=AC GC AC, the classical chip C(2) would identify the complete set of four 2-mers {AC, CA, CG, GC}. Out of the $4^2=16$ possible concatenations of these 2-mers, only eight contain a positive 2-mer as the central substring, specifically {AC AC, AC GC, CA CA, CA CG, CG CA, CG CG, GC AC, GC GC}. These could be asked in two rounds of at least 4 probes each, or one round of 8 probes.

The Adaptive Length Algorithm—This algorithm is a version of the expected $O(\log_2 n)$ round algorithm discussed below. It is essentially analogous to constructing all length l'-strings consistent with the set of all 1-substrings of S, where l'>l. Instead of setting l'=2l, as in the doubling algorithm above, the longest l' is found such that at most c·n length l' probes are consistent with the set of 1-substrings of S. Each such metaround is simulated by at most c rounds of n probes, except for the special case where l'=l+1, and α rounds may be required. Note that l' may grow very rapidly. Were the first stage to ask only length-one questions, the second stage probes would typically be $\log_c n$ in length.

For an example, consider S=ACGCAC and c=2. Although there are eight 4-mers consistent with the four 2-mers of S, there are only 12 such consistent 5-mers, specifically {AC ACA, AC ACG, AC GCA, AC GCG, CA CAC, CA CGC, CG CAC, CG CGC, GC ACA, GC ACG, GC GCA, GC GCG}. These can be asked in c=2 rounds of |S|=6 probes each.

Certain details are necessary for an efficient implementation of the adaptive length algorithm for long strings. c=2 minimizes the number of rounds for both α=2 and α=4. A one-sided binary search procedure may be used to search for l' from 1, and a linear-space suffix-tree data structure to quickly establish the necessity of a prospective probe.

Both of these algorithms for designing custom sequencing chips for interactive SBH have been implemented and simulated on DNA sequences from GenBank as well as random strings. In these experiments, up to n oligonucleotide probes are used in each simulated round, where n is the length of fragment to be sequenced. To calibrate these results for smaller size chips, observe that c·k rounds suffice using a chip of size n/c if k rounds suffice for a chip of size n. To calibrate these results for larger size chips, observe that the number of rounds can only decrease as the size of the chip increases.

Figure 4:
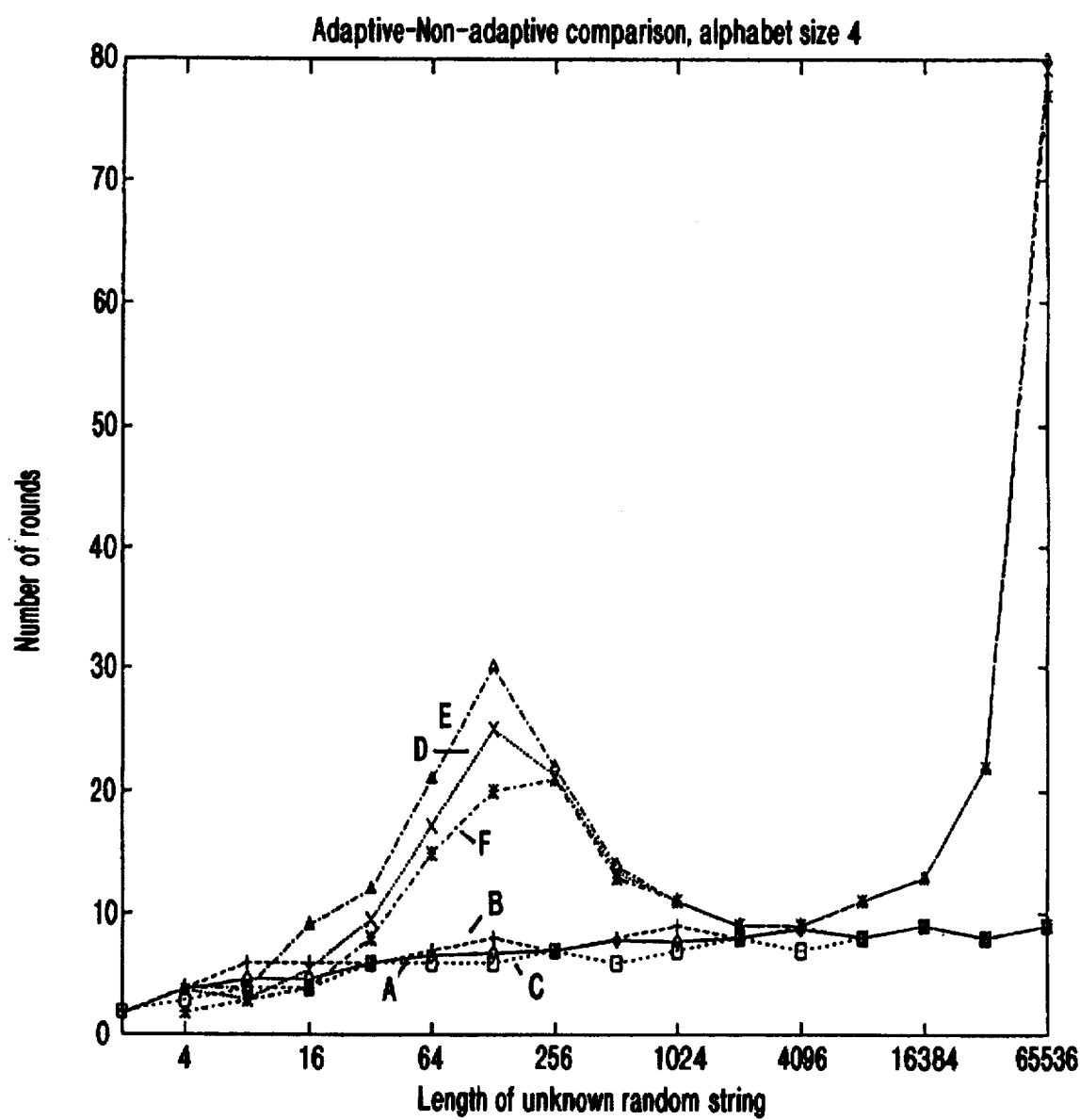
FIG. 4 shows the performance of two different adaptive probe algorithms on sequences over 4-letter alphabets, as is the case with DNA. The letters A, B, C, D, E, and F refer to the average number of rounds for the adaptive algorithm, the maximum number of rounds for the adaptive algorithm, the minimum number of rounds for the adaptive algorithm, the average number of rounds for the non-adaptive algorithm, the maximum number of rounds for the non-adaptive algorithm, and the minimum number of rounds for the non-adaptive algorithm, respectively.

These algorithms are evaluated for use as a process step on both simulated and real sequences in FIGS. 3 and 4, showing the number of rounds required for both algorithms to determine random binary and quadrary strings of length $2^i$, for $2 \leq i \leq 16$. In FIGS. 3 and 4, the letters A, B, C, D, E, and F refer to the average number of rounds for the adaptive algorithm, the maximum number of rounds for the adaptive algorithm, the minimum number of rounds for the adaptive algorithm, the average number of rounds for the non-adaptive algorithm, the maximum number of rounds for the non-adaptive algorithm, and the minimum number of rounds for the non-adaptive algorithm, respectively. For each size and algorithm, ten random strings were 'sequenced'. For each algorithm, three curves are provided, showing the maximum, average, and minimum number of rounds used. It is clear that the number of rounds required for the adaptive-length algorithm is growing

TABLE 2

Performance of The Adaptive Algorithm on GenBank Sequences.

| Sequence | Length | Rounds | Total Oligos |
|---|---|---|---|
| Human alpha globin | 12,847 | 12 | 125,546 |
| Human beta globin | 18,060 | 11 | 167,722 |
| Chicken collagen | 21,180 | 9 | 153,836 |
| Human immunodeficiency virus | 9,718 | 11 | 83,954 |
| Bacteriophage lambda | 48,502 | 11 | 386,218 |
| Mouse mitochondrion | 16,295 | 10 | 120,030 |
| Rat myosin heavy chain gene | 25,759 | 11 | 235,652 |
| Rabies virus | 11,928 | 11 | 99,167 |
| Human rhinovirus type 14 | 7,212 | 9 | 52,634 |
| Human Ribosomal DNA | 42,999 | 16 | 573,014 |
| Simian Virus 40 | 5,243 | 11 | 48,003 |
| Drosophila white locus | 14,245 | 10 | 113,202 | extremely slowly. The number of rounds is essentially a small constant for imaginable values of n, which bodes well for the potential of interactive SBH.

The number of rounds used by the doubling algorithm in FIGS. 3 and 4 demonstrates a startling degree of non-monotonicity, ie. long strings can require substantially fewer rounds to sequence than short strings. This cycling depends upon the value of $\Delta = \log_\alpha n - \lfloor \log_\alpha n \rfloor$. Since almost all $\alpha^{\log_\alpha n}$ ($\log_\alpha n$)-strings are likely to occur as substrings of S, a large fraction of the $O(n^2)$ possible concatenations will survive (for $\Delta \approx 0$) to be asked as probes in the next round. It is this behavior that the 'walking' steps discussed below was designed to avoid, although it seems apparent that even with walking the second algorithm will lead to fewer rounds of experiments at a cost of additional computation.

Table 2 reports on the number of rounds required to determine actual DNA sequences, as drawn from GenBank. The number of rounds required for actual DNA sequences seems to be slightly larger than for random data, presumably because of longer repeat sequences in DNA. However, a dozen rounds suffice to sequence all but one of the DNA sequences in this test, still very modest considering the small sizes of the sequencing chips required. The total number of probes given in Table 2 is less than the product of the number of rounds by the maximum number of questions allowed per round, because not all rounds need be filled to capacity. Thus such simulations demonstrate the potential of interactive sequencing by hybridization to sequence large DNA fragments using few rounds of customized oligonucleotide arrays, thereby demonstrating that this invention of interactive SBH provides improved de novo sequencing for large fragments.

In our paper, Skiena and Sundaram *J. Computational Biology* 2 333–353 (1995), which is incorporated by reference, studied the complexity of sequentially reconstructing unknown strings from substring queries. Specifically, they show that $(\alpha-1)n + \Theta(\alpha\sqrt{n})$ queries are sufficient to reconstruct an unknown string, where $\alpha$ is the alphabet size and n the length of the string, matching the information-theoretic lower bound for binary strings. Further, they show that approximately $\alpha n/4$ queries are necessary, which is within a factor of 4 of the upper bound for larger alphabets. However, achieving a high degree of parallelism is critical for this approach to lead to a practical method of DNA sequencing.

More recently, I have shown a wide range of tradeoffs between the number of rounds of substring probes and the number of probes per round sufficient to determine an unknown string of length n on an alphabet of size $\alpha$. The results are summarized in the table below:

| Number of Rounds | Questions per Round |
|---|---|
| $\alpha n$ | 1 |
| n | $\alpha$ |
| $\lg^2 n$ | n |
| $\lg n$ | $n^2/\lg n$ |
| $\lg \lg n$ | $\alpha^{\alpha(1+o(1))(\lg n/\lg \lg n)}$ |
| 2 | $\alpha^{O(\sqrt{n \lg n})}$ |
| 1 | $3\alpha^{\lfloor n/2 \rfloor + 1}$ |

Each of these tradeoffs require different ideas to achieve.

The case of one round is the problem of reconstructing strings using a fixed set of probes, as in conventional SBH. A sequencing chip C is defined by a given set of probe strings $c_1, \ldots, c_m$ over a given alphabet $\Sigma$. The capacity or size m of the chip is the number of strings which define it. The spectrum Sp(C,S) of chip C with respect to string S partitions the strings of C into two sets, those which are substrings of S and those which are not. A string S can be reconstructed with a given chip C if and only if there does not exist a string S' $\in \Sigma^*$ such that Sp(C,S)=Sp(C,S'). In other words, the spectrum of S uniquely describes S.

Now is considered the question of minimizing the size of any chip capable of reconstructing all strings of length n. Clearly, a chip containing all $\alpha^n$ strings of length n suffices for reconstruction, since the spectrum of any string S will contain only one positive substring, ie. S itself. However, significantly smaller chips are in fact possible.

Consider a classical sequencing chip C(l), where $l = \lfloor n/2 \rfloor + 1$, consisting of all $\alpha^l$ l-strings. A string S has period k if $S_i = S_{i+k}$ for all $1 \leq i \leq n-k$. Observe that strings of period $k \leq l$ cannot be reconstructed using C(l). For example, the strings abcdabc, bcdabcd, cdabcda, and dabcdab all contain exactly the same set of 4-substrings: abcd, bcda, cdab, and dabc. Thus C(l) does not suffice for reconstructing n-strings, but a slightly larger chip does while no smaller chip can.

In fact, the classical chip C(m) suffices to reconstruct any n-string of period k>m if m>n/2, as can be proven using results on periods of strings. Thus an array consisting of one round of $3\alpha^{\lfloor n/2 \rfloor + 1}$ probes suffices to reconstruct any n-string on an alphabet $\Sigma$, $\alpha = |\Sigma|$. It consists of all distinct $(\lfloor n/2 \rfloor + 1)$-strings, plus all n-strings of period at most $(\lfloor n/2 \rfloor + 1)$.

That no significantly smaller array suffices follows from the fact that any sequencing chip capable of reconstructing all strings of length n must have size at least $2\alpha^{\lfloor n/2 \rfloor + 1}/n - 1$.

To illustrate how interaction can be used to reduce the total number of probes in the step of selecting subsequent probes, consider reconstructing strings with one substring probe per round. A subtlety of the problem is whether the length of the unknown string is presented in advance, or must be determined using the results of probes. For ease of exposition, assume that the length n is known, since it results in simpler strategies whose complexities are identical except for lower order terms.

An unknown string S of known length n on alphabet $\Sigma$, $|\Sigma| = \alpha$ can be reconstructed in $\alpha(n+1)$ substring probes. Begin by making substring probes of single-character substrings, so after at most $\alpha$ probes a character of S is known. Let s be a known substring of S and $\Sigma = \{\sigma_1, \sigma_2, \ldots, \sigma_\alpha\}$. In general, the length of this known substring can be increased by one character by probing on the strings $s\sigma_i$, for $1 \leq i \leq \alpha$. At least one of these probe strings must be a substring of S, unless s is a suffix of S. When s can no longer be extended, s is a suffix of S and the process continues by prepending each character to the known substring, until it is of length n and S is determined.

This strategy can be parallelized in a weak and trivial way, by observing that each of the $\alpha$ extension probes can be done in parallel. However, a stronger divide-and-conquer approach is needed to deliver a much higher degree of parallelism. Consider the following r round reconstruction strategy, which is parameterized by the constants $k_1, \ldots, k_r$:

round 1: Probe all $\alpha^{n/k_1}$ strings of length $n/k_1$. Let $S_1$ denote the resulting set of substrings of S of length n $/k_1$.

round $2 \leq i \leq r$: Let $S_{i-1}$ denote the set of all of the (at most n) distinct $(\prod_{j=2}^{i-1} k_j \cdot (n/k_1))$-substrings of S. Probe all of the $n^{k_i}$ strings which can be formed as a sequence of $k_i$ elements of $S_{i-1}$.

This strategy is correct whenever $\prod_{j=2}^{r} k_j/k_1 \geq 1$, as $S_i$ is determined at the end of round i, and $S_r = S$. Select $k_1$ and $k_j$ ($2 \leq j \leq r$) to satisfy the following relations:

$$n/k_1 = \lg n \cdot k_j$$

$$k_1 = k_j^{r-1}$$

Solving for $k_1$ and $k_j$ yields:

$$k_1 = (n/\lg n)^{(r-1)/r}$$

$$k_j = (n/\lg n)^{1/r}$$

Special cases of interest which fall out of this divide and conquer approach include using 2 rounds of $\alpha^{\theta(\sqrt{n \lg n})}$ probes per round, using lg lg n rounds of $\alpha^{\alpha(1+o(1))(\lg n/\lg \lg n)}$ probes per round, and using lg n rounds of $n^\alpha$ probes per round.

The results thus far demonstrate that it is possible to reconstruct strings from substrings in few rounds, but at a cost of an exponential number of probes per round. Practical implementation of interactive SBH forbids such extravagance—the largest currently realized sequencing chip contains only 65,384 oligonucleotides. An important goal to reconstruct long sequences with chips of capacity on this order of magnitude. Below are strategies which use a polylogarithmic number of rounds, but a low-order polynomial number of probes per round. These algorithms are based on the following observations:

A string S of length n contains $\leq n-l+1$ different substrings of length l.

Given the set of all distinct l-substrings of S, $|S|=n$, one round of $(n-l+1)^2$ probes suffice to find all distinct 2l-substrings This immediately gives an algorithm for reconstructing strings in $\lceil \lg n \rceil$ rounds of $n^2$ probes, by starting with one character probes and repeatedly doubling. This strategy may be seen as wasteful, however, since some of the $n^2$ concatenations may contain l-strings which are not l-substrings of S. These prospective probes can be eliminated without affecting the accuracy of the algorithm.

This can be done by using the previously described doubling strategy, where probes are formed by concatenating two l-substrings if and only if all l distinct l-substrings of the length 2l probes are in fact substrings of S. Thus the algorithm proceeds in lg n meta-rounds, where the ith meta-round consists of $m_i$ probes surviving from at most $n-2^i-1$ candidates. If restricted to rounds of $n^2/\lg n$ probes, the total number of rounds in this strategy is given by $$R = \sum_{i=1}^{\lg n} \lceil m_i/(n^2/\lg n) \rceil$$

A no-probe asked in round i corresponds to the concatenation xy of two $2^{i-1}$-substrings of S, where x ends at position p(x) in S, y begins at position p(y) in S, and $p(x) \neq p(y)$. In no subsequent round, will a probe be asked concatenating a string ending in p(x) with a string beginning in p(y), because such a probe will contain xy, which is known not to be a substring of S. Thus at most $n^2$ probes will prove to be no-probes, and $$\sum_{i=1}^{\lg n} m_i = n^2 + n \log n$$

Subject to this contraint, R is maximized at $2 \lg n$, giving the result that O (lg n) rounds of $n^2/\lg n$ substring probes per round suffice to reconstruct any string of length n on an alphabet of size a $\alpha \leq n$.

This gets to a tradeoff approaching practicality, but $n^2/\log n$ probes per round still appears too large to sequence long pieces of DNA. For n>1000, the capacity of the largest sequencing chip constructed to date is exceeded. Below, efficient strategies using a linear number of probes per round are considered.

These techniques are based on finding efficient splitters of sets of probes. Consider a set U of m strings on alphabet $\Sigma$, $|\Sigma|=\alpha$, where each string begins with the same substring s. There exists a string s' which is contained in at least $m/(2\alpha+1)$ and at most $2m\alpha/(2\alpha+1)$ strings of U.

Because of such splitters, given the set of all distinct l-substrings of S, $|S|=n$, $(\log_{(1+\alpha/\alpha)n})$ rounds of n probes suffice to find all distinct 2l-substrings of S. Construct the set of $\leq n^2$ concatenation strings xy, and distribute them into $\leq n$ piles, where pile p(x) consists of all concatenation strings beginning with the same initial l-substring x.

For each pile, use a splitter to identify a string $q_1$ which which partitions the pile into two smaller but roughly equal-sized piles, $p_{1y}(x)$ containing $q_1$ and $p_{1n}(x)$ not containing $q_1$.

Applying a splitter to each of these piles yields a total of two more probe strings ($q_2$. for and $p_{1y}(x)$ and $q_3$ for $p_{1n}(x)$) for which partitions p(x) into four roughly equal-size piles. There are eight possible outcomes to the set of probes $q_1, q_2$, and $q_3$. If $q_1$ returns false, all of the candidates in pile $p_{1y}(x)$ can be eliminated, as all of these contain $q_1$ where S does not. This test is not symmetrical, however. If $q_1$ returns true, the algorithm cannot eliminate the candidates of $p_{1n}(x)$, because all that has been proven is that S must contain $q_1$ somewhere but this does not preclude it from containing substrings in pile $p_{1n}(x)$.

If either of probes $q_2$ or $q_3$ return false, all the candidates in at least one subpile can be eliminated, reducing the size of the original pile by a constant fraction. All three probes return true only if there exist at least two distinct substrings in S beginning with x, with one in $p_{1y}(x)$ and another in $p_{1n}(x)$.

Thus after three probes per pile, each pile is either reduced by a constant fraction or split into roughly equal subpiles. Each subpile is defined by a substring starting from a unique position in S, so there can never be more than n active subpiles. Thus in O (lg n) rounds of n probes per round, each pile can be can be reduced to at most one string per pile, each corresponding to a distinct 2l-substring of S. Further, each of the 2l-substrings must represented by a pile if the given set of l-substrings was indeed complete.

Performing the lg n meta-round doubling strategy with the pruning implementation described above shows that O (lg $n \cdot \log_{(1+\alpha)/\alpha)}n$) rounds of n substring probes per round suffice to reconstruct a string S of length n Although the algorithms described so far guarantee that the DNA sequence will be uniquely identified after the sequence of experiments, an alternate approach would be to design arrays that work with high probability. Consider the expected number of rounds to determine a random n-string when are allowed to make n probes per round. The following simple probabilistic algorithm shows that O (lg n) rounds suffice for random strings with high probability.

The key issue in this kind of analysis is the probability that an arbitrary l-string is a substring of a random n-string. Because of clustering effects for low-period strings, (for example, the string $0^x$ is likely to occur more than once in a binary string if it occurs at all) the probability that a given string s occurs in a random n-string is a function of s, not just the length of s. Simple counting arguments show that the probability goes to zero for l-strings where $l \geq (1+\epsilon) \log_\alpha n$ and to one for $l \leq (1-\epsilon) \log_\alpha n$.

Let S be a random n-string on an alphabet of size $\alpha$. With a probability of $1-1/n^\epsilon$, S can be determined using O ($\alpha \cdot \epsilon \log_\alpha n$) rounds of n probes per round. Use the following three-phase strategy to determine S. First, use one round of n probes to implement the classical sequencing chip $C(\lfloor \log_\alpha n \rfloor)$, thus determining all $\leq n$ distinct $(\log_\alpha n)$-substrings of S. Second, use $\alpha \cdot \epsilon \log_\alpha n$ rounds to 'grow' each of these strings to length $l=(1+\epsilon) \log_\alpha n$ using the technique extending each string by one character in $\alpha$ rounds. Finally, perform the doubling strategy to complete the determination of S, starting from the set of l-substrings.

The remaining issue is to analyze the number of questions asked in the first round of the third phase. Since O (n) of the concatenations correspond to actual 2l-substrings of S, all of these questions must be asked, plus any of the O ($n^2$) 'false' questions which happen to have all l-substrings occur in S.

Consider refraining from asking the 'false' questions xy whose central l-substring s is not in S. There are three different cases where s is in X but xy is not—(1) the l/2 characters after x form s with x, (2) the l/2 characters before y form s with y, and (3) s occurs elsewhere in S, not flanked by x or y. Cases (1) and (2) each occur with probability $\alpha^{l/2}$, while case (3) occurs with probability $\alpha^l$. Thus the expected number of 'false' questions to survive to the first doubling is $2n^2/n^{(1+\epsilon)}$, which is sublinear for $\epsilon > 1$. Thus an expected O (n) questions need to be asked in the first doubling round, which can simulated using a constant number of rounds of n questions. Further, the expected number of false questions decreases in subsequent doubling rounds, so O(lg n) rounds of n questions suffices for this last stage.

In fact, it is obvious that fewer rounds on average should suffice, since the concatenation of two l-strings should go unasked if any of its l-substrings is not in S, instead of just the middle one. The lack of independence makes the analysis of this difficult; however, the simulation results presented above show that this procedure to select subsequent sets of nucleic acid probes provides unexpected advantages for the invention.

Although the present invention has been described in considerable detail with reference to certain preferred versions thereof, other versions are possible, for example by using different combinatorial reconstruction algorithms, different technologies to fabricate hybridization arrays, and different biochemistry to facilitate or detect hybridizations. Therefore, the spirit and scope of the appended claims should not be limited to the description of the preferred versions contained herein, but by the appended claims and their legal equivalents.

---

---

I claim:

1. A method of identifying a sequence of a nucleic acid target, said method comprising:
    (a) providing a first set of nucleic acid probes;
    (b) hybridizing said target with said first set;
    (c) identifying any probe(s) of said first set which is(are) positively and negatively hybridized with said target, said any positively hybridized probe(s) forming a first subset;
    (d) utilizing said first set and said first subset so as to select a second set of probes wherein said second set of probes contains within the nucleic acid sequence of the second set of probes at least a portion of the nucleic acid sequence of the positively hybridized probes of the first set;
    (e) providing said second set of probes;
    (g) identifying any probe(s) of said second set which is(are) positively and negatively hybridized with said target, said any positively hybridized probe(s) of said second set forming a second subset; and
    (h) utilizing said first and second sets and said first and second subsets so as to determine the sequence of said target.

2. The method of claim 1 further comprising:
    (a) utilizing at least one of said first and second sets and said first and second subsets so as to select a third set of probes wherein said third set of probes contains within the nucleic acid sequence of the third set of probes at least a portion of the nucleic acid sequence of the positively hybridized probes of the first and second sets;

(b) providing said third set of probes;

(c) hybridizing said target with said third set;

(d) identifying any probe(s) of said third set which is(are) positively and negatively hybridized with said target, said any positively hybridized probe(s) of said third set forming a third subset; and (e) utilizing said first, second and third sets and said first, second and third subsets so as to determine the sequence of said target.

3. The method of claim 1 further comprising providing a substrate and affixing at least a fraction of the probe sets to said substrate.

4. The method of claim 1 further comprising providing a substrate, affixing said target to said substrate, and offering said probe sets to said substrate.

5. The method of claim 1 further comprising identifying non-redundant probes, said second set of probes having been selected to include said non-redundant probes.

6. The method of claim 5 wherein a combinatorial algorithm selects all probes which can be a priori identified as being positively hybridized or a priori identified as being negatively hybridized, said redundant probes being eliminated from the second set.

7. The method of claim 5 wherein said second set of non-redundant probes are partitioned into non-redundant sets to facilitate providing the probes.

8. The method of claim 5 wherein said non-redundant probes are symbolically represented by A+B (A concatenated with B), said non-redundant probes comprising all probes of a given length of the form A concatenated with B, where A is a positively hybridized probe and B is a positively hybridized probe, said probes having been selected to contain no negatively hybridized probes.

9. The method of claim 5 wherein said non-redundant probes are symbolically represented by AB, said non-redundant probes comprising all probes of a given length of the form A overlaps B, where A is a positively hybridized probe and B is a positively hybridized probe, said probes having been selected to contain no negatively hybridized probes.

10. The method of claim 5 wherein said non-redundant probes are symbolically represented by A/B, said non-redundant probes comprising all probes of a given length of the form A followed by B, where A is a positively hybridized probe and B is a positively hybridized probe, said probes having been selected to contain no negatively hybridized probes.

11. The method of claim 5 wherein said non-redundant probes are symbolically represented by A/B, said non-redundant probes comprising all probes of a given range of lengths of the form A followed by B, where A is a positively hybridized probe and B is a positively hybridized probe, said probes having been selected to contain no negatively hybridized probes.

12. The method of claim 5 wherein said non-redundant probes are symbolically represented by A/B, said non-redundant probes comprising all probes A followed by B, where A is a positively hybridized probe and B is a single nucleotide, said such probes having been selected to contain no negatively hybridized probes.

13. The method of claim 5 further comprising providing a subgraph of a de Bruijn graph, said non-redundant probes having been identified by all paths across junction vertices in the said subgraph of de Bruijn graph defined by positively and negatively hybridized probes.

14. The method of claim 5 further comprising the inclusion of selected redundant probes to detect and/or correct for hybridization errors.

* * * * *